United States Patent [19]
Gold

[11] 3,987,182
[45] Oct. 19, 1976

[54] NOVEL BENZIMIDAZOLES USEFUL AS ANTI-ANDROGENS

[75] Inventor: Elijah H. Gold, West Orange, N.J.

[73] Assignee: Schering Corporation, Kenilworth, N.J.

[22] Filed: June 9, 1975

[21] Appl. No.: 585,158

Related U.S. Application Data

[60] Continuation of Ser. No. 480,437, June 17, 1974, abandoned, which is a continuation-in-part of Ser. No. 278,913, Aug. 9, 1972, abandoned, which is a division of Ser. No. 48,466, June 22, 1970, abandoned.

[52] U.S. Cl. ............................................... 424/273
[51] Int. Cl.² ...................................... A61K 31/415
[58] Field of Search ..................................... 424/273

[56] References Cited
UNITED STATES PATENTS

| | | | |
|---|---|---|---|
| 3,317,554 | 5/1967 | Goldsmith et al. | 260/309.2 |
| 3,325,271 | 6/1967 | Goldsmith et al. | 260/309.2 |
| 3,652,580 | 3/1972 | Janiak et al. | 260/309.2 |

FOREIGN PATENTS OR APPLICATIONS

| | | | |
|---|---|---|---|
| 1,426,887 | 12/1965 | France | 260/309.2 |
| 90,296 | 10/1967 | France | 260/309.2 |
| 1,022,659 | 6/1964 | United Kingdom | 260/309.2 |
| 1,111,905 | 5/1968 | United Kingdom | 260/309.2 |

Primary Examiner—Jerome D. Goldberg
Attorney, Agent, or Firm—Raymond A. McDonald; Stephen B. Coan

[57] ABSTRACT

Disclosed herein are chemical compounds identifiable as substituted 2-alkylbenzimidazoles particularly useful as anti-androgens.

15 Claims, No Drawings

NOVEL BENZIMIDAZOLES USEFUL AS ANTI-ANDROGENS

This application is a continuation application of application Ser. No. 480,437, filed June 17, 1974 now abandoned, which in turn is continuation-in-part of application Ser. No. 278,913, filed Aug. 9, 1972 (now abandoned), which in turn is a division of application Ser. No. 48,466, filed June 22, 1970 (now abandoned).

This invention relates to therapeutically active chemical compositions belonging to the general class of substituted 2-alkylbenzimidazoles, and to the preparation and therapeutic use thereof.

The invention sought to be patented in one of its composition of matter aspects is described as residing in the concept of chemical compositions having the common molecular structure of a substituted 2-alkyl-benzimidazole.

In another of its composition of matter aspects, the invention sought to be patented resides in the concept of a therapeutically effective quantity of a compound of the invention in admixture with a suitable pharmaceutical carrier.

The invention sought to be patented in its process aspect resides in the concept of administering the tangible embodiments of the compositions of this invention in admixture with a suitable pharmaceutical carrier to elicit an anti-androgenic effect for treating benign hypertrophy in an animal species.

The tangible embodiments of this invention may be represented as substituted 2-alkylbenzimidazole of the structural formula:

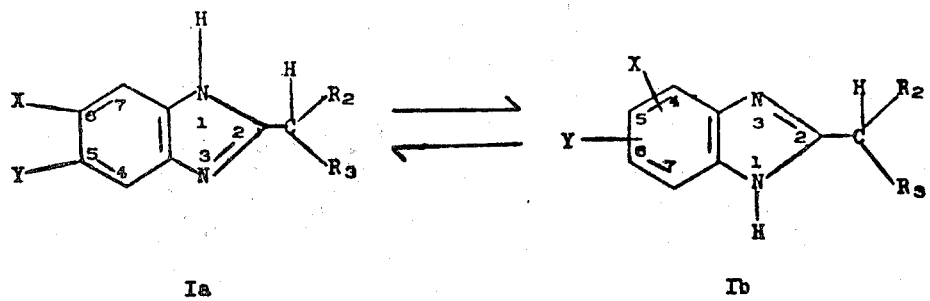

I wherein X and Y each are members selected from the group consisting of nitro, polyfluoroalkyl, and halogeno; $R_1$ is a member selected from the group consisting of hydrogen and alkyl, and $R_2$ and $R_3$ are alkyl and may form, when taken together with the carbon atom to which they are attached, a saturated cyclo alkyl radical having 3 to 4 carbon atoms.

As with any class of substituents, there are those substituents which are preferred to other members of the class. The preferred $R_1$ substituents are hydrogen and lower alkyl, preferably methyl. The preferred polyfluoroalkyl radicals are the polyfluoroloweralkyl radicals such as trifluoromethyl and difluoromethyl. Preferably $R_2$ and $R_3$ are methyl, the preferred $R_2$ and $R_3$ moieties when taken together with the carbon atom to which they are attached is cyclopropyl. Preferred X and Y substituents are when at least one in nitro, preferably in combination with trifluoromethyl.

It should of course be realized that in those instances when $R_1$ is hydrogen, the compounds of this invention exist in an equilibrium state which may be represented by the following equilibrium expression:

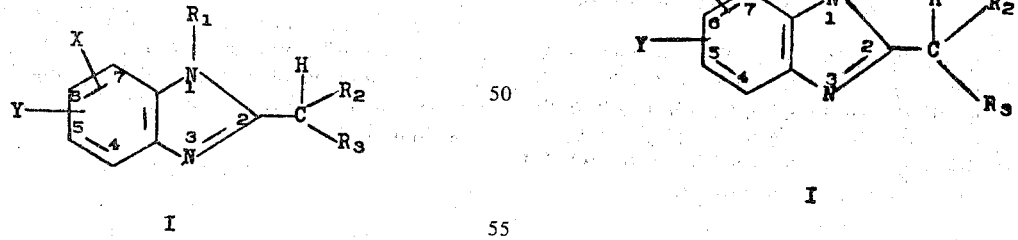

Ia                    Ib wherein X, Y, $R_2$ and $R_3$ are as previously defined. Both tautomeric forms are contemplated as being within the scope of this invention and this equilibrium will hereinafter be understood when one of the tautomers is referred to.

The nomenclature relating to this class of compounds and the numbering system used in relation thereto are a function of the position of the double bond in the imidazole portion of the molecule, and the numbering system is as follows:

I

It is then apparent that, for example, when naming a compound with 3 substituents having $R_1$ equal to hydrogen there will be two numberings possible depending upon the equilibrium state of the moiety. Exemplifying this would be a compound of the formula:

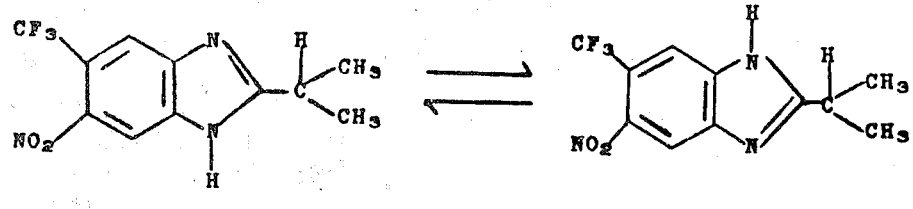

Ib                    Ic which may be named in the case of Ib: 2-isopropyl-6-nitro-5-trifluoromethylbenzimidazole and in the case of Ic: 2-isopropyl-5-nitro-6-trifluoromethylbenzimidazole.

Preferentially, the desired compounds are prepared by the cyclization of an o-aminocarboxanilide or by selectively substituting a benzimidazole nucleus.

When the starting material is a benzimidazole, the selective substitution of any of the X, Y, $R_1$, $R_2$ or $R_3$ substituents may be effected by standard procedures for their introduction into such a molecule.

Reaction Scheme I depicts the preparation of a disubstituted benzimidazole wherein the monosubstituted benzimidazole is reacted with nitric acid and sulfuric acid. Upon completion of the reaction, a process requiring several hours, the reaction mixture is neutralized with such reagents as sodium hydroxide and sodium bicarbonate and then the benzimidazole is extracted by methods well known to the art such as with ether or with other suitable non-reactive solvents and recrystallized from an organic solvent such as benzene.

REACTION SCHEME I

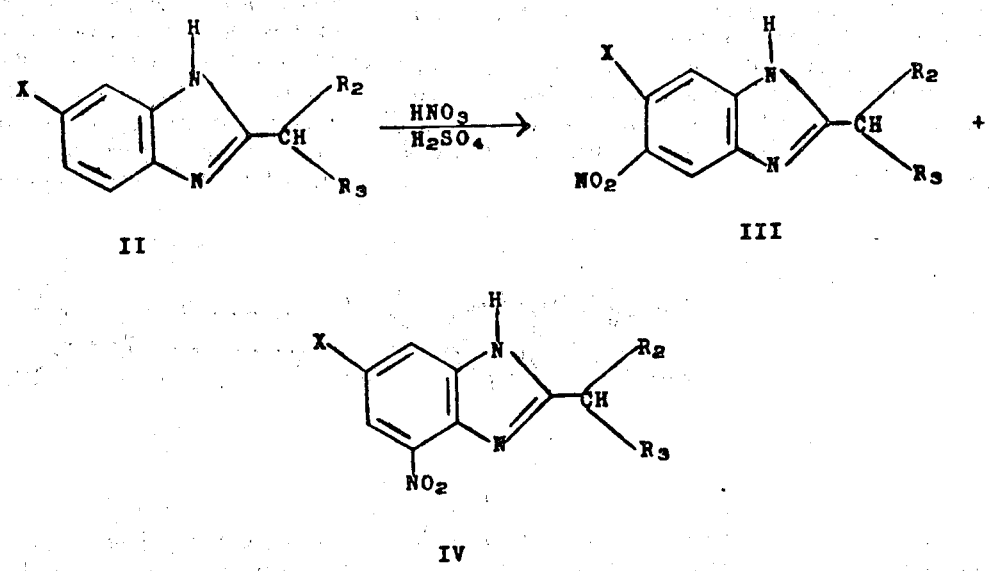

The cyclization for the o-aminocarboxanilide may be effected by subjecting the carboxanilide to elevated temperatures. The reaction may be conducted in the presence of a non-reactive solvent such as xylene, cymene or dimethylformamide. The resultant benzimidazole may be purified by methods well known to the art such as sublimation.

The desired o-amino-carboxanilide starting materials may be prepared from a corresponding o-nitro-carboxanilide. The o-nitro-carboxanilide may be reduced to the o-amino-derivatives by a reaction with a reducing agent such as stannic chloride, palladium on carbon and the like.

In those instances wherein the desired starting material is not specifically described in the literature, such reactants may be prepared according to known methods suitable for preparing such starting materials.

Reaction Schemes I and II exemplify processes for preparing composition of this invention.

wherein X, $R_2$ and $R_3$ are as previously defined. The separation of components III and IV may be accomplished by standard methods.

Reaction Scheme II depicts the preparation of a disubstituted-N-alkylated-2-alkylbenzimidazole from a trisubstituted-o-nitrocarboxanilide (V). The o-nitrocarboxanilide (V) is reacted in a suitable solvent with sodium hydride and an alkylhalide giving the N-alkylated o-nitrocarboxanilide (VI). Then, VI is subjected to a reducing agent converting the o-nitro to an o-amino, and ring closure is effected giving the desired benzimidazole which is separated and purified by standard methods.

REACTION SCHEME II

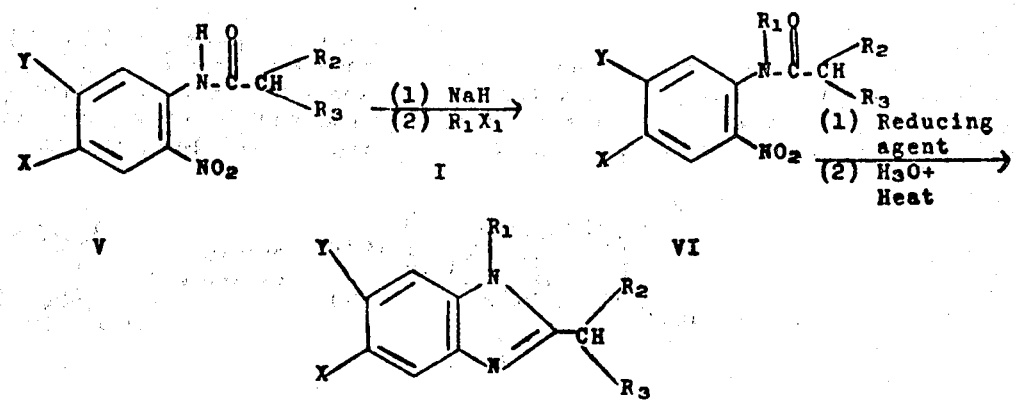

wherein $R_1$, $R_2$ and $R_3$ are as previously defined and $X_1$ is halogen, preferably iodine or bromine. X and Y are as previously defined but with the proviso that when this reaction is used they may not equal nitro.

In those instances wherein X is halogen it is preferable to use a route of synthesis not employing catalytic reducing agents such as palladium on carbon.

Furthermore, the substituted 2-alkylbenzimidazoles of this invention may be prepared by several other procedures exemplified by the following known reactions for the preparations of benzimidazoles.

A. The reaction of an ortho-aminoaniline with an acid chloride in a non-reactive organic solvent such as xylene or benzene at elevated temperatures, up to that of reflux;

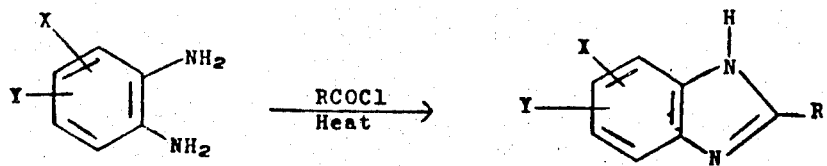

wherein X and Y are as previously defined and R represents the desired 2-substituent.

B. The cyclization of a substituted 2-aminocarboxanilide by heating in the presence of an acid and a non-reactive solvent.

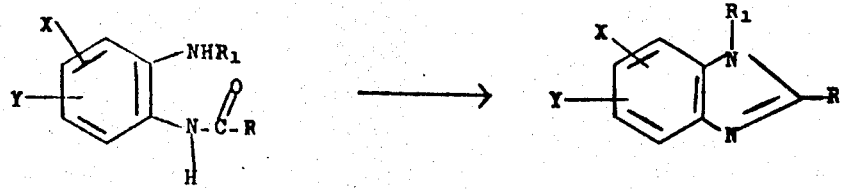

wherein X, Y, $R_1$ and R are as previously defined.

C. The condensation and cyclization of an o-dinitro benzene and a carboxylic acid in the presence of an acid, such as hydrochloric acid and a reducing agent such as stanning chloride:

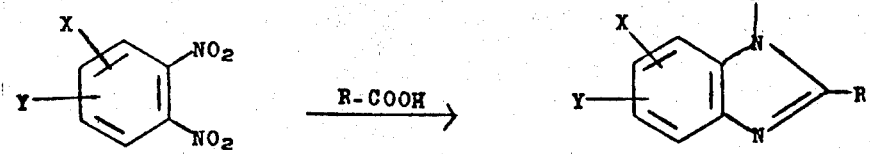

It should be realized that in this example X and Y cannot equal nitro.

It is understood that the hereinabove described reactions may be conducted in a similar manner by beginnig with substituted or mono-substituted moieties. The desired substitutions may, in these cases, be subsequently added by standard chemical procedures.

The following examples are illustrative of the processes for the preparation on representative compounds of the invention.

EXAMPLE 1

2-Isopropyl-5(6)-nitro-6(5)-trifluoromethylbenzimidazole

A. 2'-nitro-4'-trifluoromethylisobutyranilide
Reflux 187.3 g. of 2-nitro-4-trifluoromethylaniline and 320 g. of isobutyric anhydride together for two hours. Remove the excess anhydride and the resulting isobutyric acid in vacuo. Recrystallize from hexane, obtaining the product of this step.

B. 2'-amino-4'-trifluoromethylisobutyranilide
Shake 85 g. of 2'-nitro-4'-trifluoromethylisobutyranilide in 1.0 liter of ethanol containing 3.0 g. of 5% palladium on charcoal in a parr shaker under approximately 50 lbs. per square inch hydrogen pressure for twenty-four hours. Filter, remove the ethanol and recrystallize from a dichloromethane-chloroform-hexane mixture, obtaining the product of this step.

C. 5(6)-trifluoromethyl-2-isopropylbenzimidazole
Under a nitrogen atmosphere, heat 6.9 g. of 2-amino-4-trifluoromethylisobutyranilide at 200° C for twenty minutes. Sublime the crude product at 180° C (0.02 mm.) obtaining the product of this step.

D. 2-isopropyl-5(6)-nitro-6(5)-trifluoromethylbenzimidazole
Slowly add 6.4 g. of 90% nitric acid dissolved in 14 ml. of concentrated sulfuric acid to a stirred solution of 18.0 g. of 2-isopropyl-5(6)-trifluoromethylbenzimidazole. Maintain the reaction mixture at a constant temperature for approximately 2 ½ hours. Pour the reaction mixture into 2 liters of ice water and add 120 g. of 50% aqueous sodium hydroxide, followed by 200 g. of sodium bicarbonate. Extract with ether and dry over sodium sulfate, evaporating to dryness. Recrystallize once from carbon tetrachloride-dichloromethane and then several times from benzene obtaining 2-isopropyl-5(6)-nitro-6(5)-trifluoromethylbenzimidazole.

EXAMPLE 2

2-Isopropyl-1-methyl-5,6-ditrifluoromethylbenzimidazole

A. 2-Nitro-4,5-ditrifluoromethylisobutyranilide
Add 6.0 g. of 3,4-ditrifluoromethylisobutyranilide to 21 ml. of fumic sulfuric acid. Add 6.75 g. of fumic nitric acid to the above solution in a dropwise manner. Stir for four hours. Pour the mixture into 150 ml. of ice water and extract with dichloromethane and wash the extract first with sodium bicarbonate and then water.

Evaporate to dryness giving 4.5 g. of the crude benzimidazole. Chromatograph, obtaining the product of this step.

B. N-Methyl-2-nitro-4,5-ditrifluoromethylisobutyranilide

Under a nitrogen atmosphere, slowly add 11.6 g. of 2-nitro-4,5-ditrifluoromethylisobutyranilide to a stirred suspension of 4.0 g. of sodium hydride (55% in mineral oil) in 100 ml. of dimethylformamide. Stir for one hour. Vacuum filter rapidly and add 14.0 g. of methyl iodide to the filtrate stirring for 1 hour. Add 500 ml. of ice-cold water extract with ether. Dry over add 14.0 of methyl iodide to the filtrate stirring for 1 hour. Add 500 ml. of ice-cold water extract with ether. Dry over sodium sulfate, filter and remove the solvent in vacuo. Wash the resultant oil in hexane, removing the entrapped mineral oil obtaining the compound of this example as an oil.

2-Isopropyl-1-methyl-5,6-ditrifluoromethylbenzimidazole

Shake 12.0 g. of N-methyl-2-nitro-4,5-ditrifluoromethylisobutyramide in 100 ml. of ethanol containing 0.3 g. of 5% palladium on carbon at an initial pressure of approximately 50 lbs. per square inch for four days. Filter, removing the solvent, and add 40 ml. of 4N hydrochloric acid and reflux for 30 minutes. Cool, basify with sodium bicarbonate and extract with ether. Dry over sodium sulfate, filter and remove solvent with ether. Dry over sodium sulfate, filter and remove solvent obtaining the compound of this example.

EXAMPLE 3

2-Isopropyl-1-methyl-5-nitro-6-trifluoromethylbenzimidazole

A. 2-Isopropyl-1-methyl-6-trifluoromethylbenzimidazole

Shake 12.0 g. of N-methyl-2'-nitro-5'-trifluoromethylisobutyranilide in 100 ml. of ethanol containing 0.3 g. of 5% palladium on carbon at an initial pressure of approximately 50 lbs. per square inch. Filter, removing the solvent, and add 40 ml. of 4N hydrochloric acid and reflux for 30 minutes. Cool, and basify with sodium bicarbonate. Extract with ether and dry over sodium sulfate. Sublime at 55° C (0.1 mm) obtaining the product of this step.

B. 2-Isopropyl-1-methyl-5-nitro-6-trifluoromethylbenzimidazole

To a stirred solution of 3.4 g. of 2-isopropyl-1-methyl-6-trifluoromethylbenzimidazole in 15 ml. of concentrated sulfuric acid at about 5° C, slowly add 1.15 g. of 90% nitric acid dissolved in 2.5 ml. of concentrated sulfuric acid. Maintain the reaction temperature at about 5° C for two hours. Pour the reaction mixture into 300 ml. of ice-water and basify with 28 ml. of 50% sodium hydroxide followed by sodium carbonate. Extract with ether, dry over sodium sulfate, filter and evaporate to dryness. Recrystallize from methylenechloride-hexane obtaining the analytically pure product of this example.

In a similar manner by substituting for the 2-isopropyl-1-methyl-6-trifluoromethylbenzimidazole reactant of this example an equivalent quantity of: 2-isovaleryl-1-butyl-6-trifluoromethylbenzimidazole, 2-cyclobutyl-1-methyl-6-difluoromethylbenzimidazole, 2-cyclopropyl-1-ethyl-6-pentafluorothylbenzimidazole, 2-isopropyl-1-hexyl-4,6-ditrifluoromethylbenzimidazole, 2-cyclopropyl-1-ethyl-6-fluorobenzimidazole, 2-isobutyl-1-methyl-6-bromobenzimidazole, there is produced: 2-isovaleryl-1-butyl-5-nitro-6-trifluoromethylbenzimidazole, 2-cyclobutyl-1-methyl-5-nitro-6-difluoromethylbenzimidazole, 2-cyclopropyl-1-ethyl-5-nitro-6-pentafluoroethylbenzimidazole, 2-isopropyl-1-hexyl-5-nitro-6-trifluoromethylbenzimidazole, and 2-isobutyl-1-methyl-5-nitro-6-bromobenzimidazole, respectively.

EXAMPLE 4

2-Isopropyl-1-methyl-6-nitro-5-trifluoromethylbenzimidazole

A. N-methyl-2-nitro-4-trifluoromethylisobutyranilide

To a stirred suspension of 13.1 g. of sodium hydride (55% in mineral oil) in 300 ml. of dimethylformamide, under a nitrogen atmosphere, slowly add 50.0 g. of 2-nitro-4-trifluoromethylisobutyranilide and stir one hour. Vacuum filter rapidly and add 35.5 g. of methyl iodide to the filtrate and stir for one hour. Add 2 liters of ice cold water, extract with ether, dry over sodium sulfate, filter, remove the solvent and obtain the desired product.

B. 2-Isopropyl-1-methyl-5-trifluoromethylbenzimidazole

Shake 42.0 g. of N-methyl-2-nitro-4-trifluoromethylisobutyranilide in 300 ml. of ethanol, containing 0.5 g. of 5% palladium on carbon at an initial pressure of 50 lbs. per square inch for four days. Filter, remove the solvent, triturate with ether several times and filter off the N-oxide of the desired benzimidazole. Remove the ether from the mother liquor, add 50 ml. of 4N hydrochloric acid and reflux for 30 minutes. Filter, basify the filtrate with concentrated ammonium hydroxide, extract with ether, dry over sodium sulfate, filter and remove the solvent. Triturate with hexane, filter, remove the solvent from the filtrate and obtain the desired benzimidazole. Sublimation at 55° C (0.1 mm) affords the analytically pure product of this example.

C. 2-Isopropyl-1-methyl-6-nitro-5-trifluoromethylbenzimidazole

Slowly add 1.01 g. of 90% nitric acid dissolved in 2.2 ml. of concentrated sulfuric acid to a stirred solution of 3.00 g. of 2-isopropyl-1-methyl-5-trifluoromethylbenzimidazole in 13.2 ml. of concentrated sulfuric at about 5° C. Maintain the reaction at about 5° C for 2 hours. Pour the reaction mixture into 300 ml. of ice water and basify with 26 ml. of 50% sodium hydroxide followed by sodium carbonate. Extract with ether, dry over sodium sulfate and evaporate to dryness. Recrystallize from dichloromethane-hexane, obtaining the product of this example.

The tangible embodiments of the compounds represented by formula I possess the inherent applied use characteristic of exerting an anti-androgenic response when administered in a dose range of about 0.1 mg/kg to about 30 mg/kg of body weight per day and thus are useful in treatment of benign prostrate hypertrophy.

The compositions of this invention are useful in treating such androgen-sensitive conditions as benign prostatic hypertrophy. In those species afflicted with benign prostatic hypertrophy, the frequency of the hypertrophy condition seems to increase with increasing age and thus represents a serious problem, even among older canine household pets. In general, hormone therapy, such as for example, administration of estrogenic substances, has not proved to be a particularly desirable treatment, not only because of the undesirable side effects due to the inherent properties of the estrogen, but also because such agents have not proved to be fully efficacious in providing meaningful remissions and cures. Surgical ablation, even though effective, is also not particularly desirable for in addition to the expected 2–3% mortality rate, many patients experience such non-fatal complications such as epididymitis, pneumonia, pyelonephritis, secondary resection, etc. Thus, the chemotherapeutic treatment of benign prostatic hypertrophy with concomitant absence of side effects induced by the anti-androgenic agent has been a goal long sought.

It has been determined by standard laboratory test procedures that the compositions of this invention produce marked remissions in cases of benign prostatic hypertrophy without the undesirable effects elicited upon the administration of estrogens or complications inherent in any surgical procedures. Usually, depending upon the severity of the condition, a satisfactory therapeutic response is achieved in those mammal species having an adult body weight of approximately 70 kg. when 1 to 4 dosage units of the hereinafter described pharmaceutical formulations are administered to the species. Thus, a suitable dosage range for a 70 kilogram mammal is in the range of about 25 mg. to 100 mg. of the preferred active composition per day.

As stated above, the compositions of this invention may be used as chemical castrating agents in the veterinary field.

It has been long known that the male androgen-containing animal species is not particularly suitable as a meat producing animal. It is also known that the male animal grows at a faster rate, usually weighs more and produces a leaner carcass than does the corresponding female species. One attempt at converting the male into a more suitable commercial meat source has been by surgical castration. However, this method has not been completely satisfactory for it involves a time-consuming process and often times leads to post-surgical problems such as infections.

Quite unexpectedly, it has been found that upon administration of a therapeutically effective quantity of the compositions of this invention (in accordance with the hereinafter described manner) the aforementioned undesirable characteristics are obviated and thus a more suitable animal species is available for commercial use. In addition to the enhanced growth characteristics, it is also found that these chemically castrated animal species are devoid of the noxious odor usually associated with such animals. This noxious odor is particularly manifested by the pig species wherein the meat of the males, upon cooking, emits the well-known and quite repugnant "boar-odor" rendering the meat product unpalatable. The meat derived from the chemically castrated animal is not so tainted and indeed, it is quite palatable. This discovery is of great economic importance, in that the previously commercially unsuitable meat products were the source of a great economic waste. Although the application of this discovery is particularly suitable for the treatment of pigs, it also may be used for treating other animal species such as cattle, horses, sheep, oxen, hogs, goats, and the like. Indeed, the compositions of this invention may also be used as chemical castrating agents for eliciting the desired effect in such avian species as drakes, geese, roosters, turkeys, and the like. The administration of the compositions being accomplished only during the development of the secondary sex characteristics as will be hereinafter described.

As chemical castrating agents, these compositions are also useful as pest control agents where the effect is to decrease the population of the undesired species by ineffectuating the male species thereof.

The hereinabove described chemical testicular castration process may be effected in two manners. In mammals, the desired effect is obtained by administering a therapeutically effective quantity of the compositions represented by formula I to a male-fetus bearing mammalian quadruped during the development of the genitalia of said fetus. The results of said administration is that the litter produced will be devoid of all male species and will consist of females and hermaphrodites. The period of gestation during which the fetal genitals develop is documented for many animal species and where such information is not available in the literature, the period may be determined by methods well known to the art.

The second process for chemically castrating a male androgen-containing animal species comprises the administration of a therapeutically effective quantity of the compositions of this invention to a male androgen-containing animal species during the development of its secondary sex characteristics so as to elicit an anti-androgenic effect during and after said period. The animal so treated will be suitable for use as a commercial source of meat. The other manifestations of the chemical testicular castration are also known in these animals.

Representative of the preferred compositions for carrying out the process aspect of this invention are:
2-isopropyl-1-methyl-5-nitro-6-trifluoromethylbenzimidazole,
2-isopropyl-5(6)-nitro-6(5)-trifluoromethylbenzimidazole,
2-cyclopropyl-1-methyl-5-nitro-6-trifluoromethylbenzimidazole,
2-cyclopropyl-5(6)-nitro-(6(5)-trifluoromethylbenzimidazole,
2-isopropyl-1-methyl-5,6-ditrifluoromethylbenzimidazole,
2-isopropyl-5,6-ditrifluoromethylbenzimidazole,
2-cyclopropyl-1-methyl-5,6-ditrifluoromethylbenzimidazole,
2-cyclopropyl-5,6-ditrifluoromethylbenzimidazole,
2-isopropyl-1-methyl-5-iodo-6-trifluoromethylbenzimidazole, and
2-isopropyl-5(6)-iodo-6(5)-trifluoromethylbenzimidazole.

The compositions of this invention can be administered orally in the form of tablets, capsules, elixirs, and the like, or may be administered by parenteral injection. In tablet form they are compounded with an inert pharmaceutical carrier which may contain a suitable binder such as, for example, gums, starches, and sugars. They may be also incorporated into gelatin capsules or formulated into elixirs which have the advantage of being susceptible to manipulations in flavor by the addition of standard natural or synthetic flavoring agents. Highly satisfactory administration may also be achieved in the form of an aqueous parenteral suspension. Furthermore, the compositions of this invention may be admixed with the food or water supply of the species to which administration is desired.

Preferably, these formulations are so proportioned as to afford a unit dose of about 1 to about 100 mg. of the substituted 2-alkylbenzimidazole. Particularly preferred are oral dosages ranging from about 5 to 25 mg.

Representative embodiments of the formulations containing the compositions of this invention are as follows:

TABLET FORMULATIONS

| Formula A (5 mg.) | Milligrams per Tablet |
|---|---|
| 2-Isopropyl-1-Methyl-5-Nitro-6-Trifluoromethylbenzimidazole | 5.0 |
| Starch, Food Grade | 5.0 |
| Lactose, U.S.P. (Spray Dried) | 89.5 |
| Magnesium Stearate, U.S.P. | 0.5 |
| | 100.0 |

| Formula B (25 mg.) | Milligrams per Tablet |
|---|---|
| 2-Isopropyl-1-Methyl-5-Nitro-6-Trifluoromethylbenzimidazole | 25.0 |
| Starch, Food Grade | 10.0 |
| Lactose, U.S.P. (Spray Dried) | 164.0 |
| Magnesium Stearate, U.S.P. | 1.0 |
| | 200.0 |

Pass the 2-isopropyl-1-methyl-5-nitro-6-trifluoromethylbenzimidazole through a high speed mill equipped with a 100 to 150 mesh screen. Blend the milled 2-isopropyl-1-methyl-5-nitro-6-trifluoromethylbenzimidazole with the starch in a suitable mixing vessel. Add an equal weight of the spray dried lactose to the blend and mix until uniform. Combine the resultant blend with the remainder of the spray dried lactose and mix until uniform. Charge the magnesium stearate with a portion of the active tablet mix and blend. Blend the magnesium stearate mix with the remaining active tablet base. Continue mixing until uniform. Compress to target weight (100.0 mg. for 5 mg. tablet and 200.0 mg. for 25 mg. tablet).

CAPSULE FORMULATIONS

| Formula | Milligrams per Capsule |
|---|---|
| 2-Isopropyl-1-Methyl-5-Nitro-6-Trifluoromethylbenzimidazole | 5.0 |
| Lactose, U.S.P. (Spray Dried) | 292.0 |
| Magnesium Stearate, U.S.P | 3.0 |
| | 300.0 |

Blend ingredients until uniformely mixed. Fill into hard gelatin capsule.

PARENTERAL SUSPENSION

| Formula A (5 mg.) | Milligrams per Milliliter |
|---|---|
| 2-Isopropyl-1-Methyl-5-Nitro-6-Trifluoromethylbenzimidazole | 5.00 |
| Methyl Cellulose 15 cps. U.S.P | 0.05 |
| Sodium Citrate, Dihydrate | 6.00 |
| Benzyl Alcohol, NF | 9.00 |
| Methylparaben, U.S.P. | 1.80 |
| Propylparaben, U.S.P. | 0.20 |
| Water for Injection, U.S.P. q.s. a.d. | 1.00 ml. |

| Formula B (25 mg.) | Milligrams per Milliliter |
|---|---|
| 2-Isopropyl-1-Methyl-5-Nitro-6-Trifluoromethylbenzimidazole | 25.00 |
| Methyl Cellulose 15 cps., U.S.P. | 0.25 |
| Sodium Citrate, Dihydrate | 30.00 |
| Benzyl Alcohol, NF | 9.00 |
| Methylparaben, U.S.P. | 1.80 |
| Propylparaben, U.S.P. | 0.20 |
| Water for Injection, U.S.P. q.s. a.d. | 1.00 |

Charge 45 liters of water for injection into a suitable stainless steel vessel and heat to 85°–90° C. With vigorous agitation, slowly sprinkle the methyl cellulose into the hot water (5 mg. for formula A or 25 for formula B). Agitate until the methyl cellulose is thoroughly dispersed and wetted. Add approximately 30 liters of cold (0°–5° C) water for injection. Cool the entire mixture to 8° C. Dissolve the sodium citrate (600 gm. of formula A or 3000 gm. for formula B) in enough water for injection to make 5 liters of solution. Slowly and with agitation add this solution to the cooled methyl cellulose solution. Dissolve the parabens (180 gm. of methyl and 20 gm. of propyl) in 900 gm. of benzyl alcohol which has been heated to 30° C. Charge this solution to the chilled methyl cellulose solution. Bring the resulting solution to 90 liters with water for injection and agitate until uniform. In a sterile area, pass the batch through a sterile filter. Asceptically transfer about 3.5 liters of the sterile methyl cellulose solution to a separate container reserving the remainder of the batch in a sterile stainless steel mixing tank. Slurry the 2-isopropyl-1-methyl-5-nitro-6-trifluoromethylbenzimidazole in a sterile colloid mill with about 2 liters of the separated methyl cellulose solution and add the slurry to the solution in the mixing tank. Rinse the slurry container and the mill with the remaining 1.5 liters of reserved methyl cellulose solution and add the rinse to the mixing tank. Rinse the slurry container and mill with 2 liters of water for injection and add the rinse to the mixing tank. Adjust the volume in the mixing tank to 100 liters with water for injection and agitate until uniform. The bath affords 100 liters of sterile suspension having the proportions for Formula A or Formula B.

I claim:

1. A process for eliciting an anti-androgenic effect for treating benign prostatic hypertrophy which comprises administering to mammals suffering from benign prostatic hypertrophy an effective quantity for treating said benign prostatic hypertrophy with a compound of the formula:

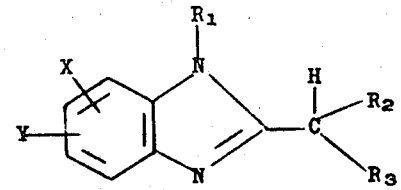

and the tautomers thereof, wherein each of Y and X is a member selected from the group consisting of nitro, polyfluoroloweralkyl and halogeno; $R_1$ is a member selected from the group consisting of hydrogen and lower alkyl; and $R_2$ and $R_3$ each are lower alkyl and when taken together with the carbon atom to which they are attached are saturated cyclo alkyl radicals having 3 to 4 carbon atoms.

2. A method of claim 1 wherein X is nitro and Y is trifluoromethyl.

3. A method of claim 1 wherein X and Y are each trifluoromethyl.

4. A method of claim 1 wherein X and Y are halogeno.

5. A method of claim 1 wherein X is halogeno and Y is trifluoromethyl.

6. A method of claim 1 wherein the compound is 2-isopropyl-1-methyl-5-nitro-6-trifluoromethylbenzimidazole.

7. A method of claim 1 wherein the compound is 2-isopropyl-5(6)-nitro-6(5)-trifluoromethylbenzimidazole.

8. A method of claim 1 wherein the compound is 2-cyclopropyl-1-methyl-5-nitro-6-trifluoromethylbenzimidazole.

9. A method of claim 1 wherein the compound is 2-cyclopropyl-5(6)-nitro-6(5)-trifluoromethylbenzimidazole.

10. A method of claim 1 wherein the compound is 2-isopropyl-1-methyl-5,6-ditrifluoromethylbenzimidazole.

11. A method of claim 1 wherein the compound is 2-isopropyl-5,6-ditrifluoromethylbenzimidazole.

12. A method of claim 1 wherein the compound is 2-cyclopropyl-1-methyl-5,6-ditrifluoromethylbenzimidazole.

13. A method of claim 1 wherein the compound is 2-cyclopropyl-5,6-ditrifluoromethylbenzimidazole.

14. A method of claim 1 wherein the compound is 2-isopropyl-1-methyl-5-iodo-6-trifluoromethylbenzimidazole.

15. A method of claim 1 wherein the compound is 2-isopropyl-5(6)-iodo-6(5)-trifluoromethylbenzimidazole.

* * * * *